(12) United States Patent
Stankowski et al.

(10) Patent No.: US 11,759,617 B2
(45) Date of Patent: Sep. 19, 2023

(54) CONNECTION CLAMPING DEVICE

(71) Applicant: Global Life Sciences Solutions USA LLC, Marlborough, MA (US)

(72) Inventors: Ralph Stankowski, Westborough, MA (US); Colin R. Tuohey, Marlborough, MA (US); Eric Tenander, Westborough, MA (US); Ethan Michael Barrieau, Marlborough, MA (US); Jonathan Kenney, Marlborough, MA (US)

(73) Assignee: Global Life Sciences Solutions USA LLC, Marlborough, MA (US)

( * ) Notice: Subject to any disclaimer, the term of this patent is extended or adjusted under 35 U.S.C. 154(b) by 373 days.

(21) Appl. No.: 16/500,009

(22) PCT Filed: Apr. 4, 2018

(86) PCT No.: PCT/EP2018/058605
§ 371 (c)(1),
(2) Date: Oct. 1, 2019

(87) PCT Pub. No.: WO2018/185161
PCT Pub. Date: Oct. 11, 2018

(65) Prior Publication Data
US 2020/0108242 A1    Apr. 9, 2020

Related U.S. Application Data

(60) Provisional application No. 62/482,016, filed on Apr. 5, 2017.

(51) Int. Cl.
*A61M 39/12* (2006.01)
*F16L 33/035* (2006.01)
(Continued)

(52) U.S. Cl.
CPC .......... *A61M 39/12* (2013.01); *F16L 33/035* (2013.01); *F16L 33/23* (2013.01);
(Continued)

(58) Field of Classification Search
CPC ..... A61M 39/12; F16L 33/23; F16L 2201/44; F16L 2201/10
See application file for complete search history.

(56) References Cited

U.S. PATENT DOCUMENTS 3,185,500 A    5/1965 Luther
3,526,416 A    9/1970 Kish
(Continued)

FOREIGN PATENT DOCUMENTS

DE    3520953 C1    9/1986
GB    968973 A    9/1964
(Continued)

OTHER PUBLICATIONS

PCT International Search Report for PCT Application No. PCT/EP2016/073545 dated Jan. 9, 2017 (8 pages).
(Continued)

*Primary Examiner* — Zachary T Dragicevich
(74) *Attorney, Agent, or Firm* — Eversheds Sutherland (US) LLP

(57) ABSTRACT

A connection clamping device (21; 61; 81; 131; 151) arranged for securing a flexible tube (1) to a barbed end (5*b*) of a tube connector (5), whereby the barbed end (5*b*) comprises a barb (9) and the tube connector during connection is arranged to protrude into an end of the flexible tube (1), characterized in that said connection clamping device comprises two sections (23 *a*, 23*b*) which, during connection when the tube connector protrudes into an end of the flexible tube, are arranged to be connected and locked to each other by a locking mechanism (33*a*,33*b*,34*a*,34*b*; 63*a*, 63*b*, 64*a*,
(Continued)

64*b*) around the tube connector (5) and the flexible tube (1), such that the flexible tube (1) is compressed against the tube connector (5) by a rib (41*a*, 41*b*) provided on the inner circumference of the connection clamping device.

18 Claims, 15 Drawing Sheets

(51) Int. Cl.
*F16L 33/23* (2006.01)
*A61M 39/10* (2006.01)
*C12M 1/00* (2006.01)

(52) U.S. Cl.
CPC ..... *A61M 2039/1066* (2013.01); *C12M 23/28* (2013.01); *F16L 2201/10* (2013.01); *F16L 2201/44* (2013.01)

(56) References Cited

U.S. PATENT DOCUMENTS

| | | | |
|---|---|---|---|
| 4,139,224 A * | 2/1979 | Leach | F16L 33/23 285/259 |
| 4,451,070 A | 5/1984 | Sauer | |
| 4,723,948 A | 2/1988 | Clark et al. | |
| 4,912,602 A | 3/1990 | Zurek et al. | |
| 5,074,600 A | 12/1991 | Weinhold | |
| 5,137,309 A | 8/1992 | Beagle | |
| 6,155,610 A | 12/2000 | Godeau et al. | |
| 7,370,889 B2 | 5/2008 | Maunder et al. | |
| 8,888,140 B2 | 11/2014 | Stroempl et al. | |
| 10,352,488 B2 | 7/2019 | Barrientos | |
| 2006/0106365 A1 | 5/2006 | Lane et al. | |
| 2008/0221469 A1 | 9/2008 | Shevchuk | |
| 2008/0319421 A1 | 12/2008 | Bizup et al. | |
| 2011/0163533 A1 | 7/2011 | Snyder et al. | |
| 2013/0060268 A1 | 3/2013 | Herrig | |
| 2013/0257041 A1 | 10/2013 | Pierce | |
| 2015/0167874 A1 | 6/2015 | Buerli et al. | |
| 2015/0308598 A1 | 10/2015 | Lewis et al. | |
| 2016/0146386 A1 | 5/2016 | Blake et al. | |
| 2018/0266600 A1 | 9/2018 | Stankowski | |
| 2020/0378530 A1 * | 12/2020 | Schneider | F16L 33/2076 |

FOREIGN PATENT DOCUMENTS

| | | |
|---|---|---|
| JP | 2006097841 A | 4/2006 |
| WO | 2006/135227 A1 | 12/2006 |
| WO | 2015/191991 A1 | 12/2015 |
| WO | 2017/060188 A1 | 4/2017 |

OTHER PUBLICATIONS

Chinese Office Action for CN Application No. 201680058469.8 dated Feb. 19, 2020 (15 pages with English translation).
Chinese Office Action for CN Application No. 201880021968.9 dated Jul. 30, 2021 (14 pages, with English translation).
European Notice of Opposition for EP Application No. 16781316.1 dated Sep. 7, 2021 (47 pages).
PCT International Search Report and Written Opinion for PCT Application No. PCT/EP2018/058605 dated Jul. 9, 2018 (12 pages).

* cited by examiner

CONNECTION CLAMPING DEVICE

CROSS REFERENCE TO RELATED APPLICATIONS

This application claims the priority benefit of PCT/EP2018/058605 filed on Apr. 4, 2018, which claims priority benefit of U.S. Provisional Patent Application No. 62/482,016 filed on Apr. 5, 2017, the entire contents of which are hereby incorporated by reference herein.

TECHNICAL FIELD OF THE INVENTION

The present invention relates to a connection clamping device for use with disposable bioprocess assemblies and to a method for securing flexible tubes to tube connectors during the manufacture of disposable bioprocess assemblies. It also relates to a disposable bioprocess assembly with one or more connection clamping devices and to a method of bioprocessing using such assemblies.

BACKGROUND OF THE INVENTION

Flexible tubing/tubes are used for transferring fluids or gases in many different environments for example in bioprocessing, medical and food industry. The flexible tubing needs to be connected to different components such as for example bags, sensors, fittings, ports or couplings of different types. Especially in for example the medical field and the bioprocessing field it is highly important that these connections are leak proof and that no liquid will get trapped in the connection causing for example growth of bacteria.

A tube connector of the coupling, port or fitting to which the flexible tube typically is connected often comprises a barb. A commonly used way to perform the connection is to simply use a cable tie around the flexible tube and the tube connector which has been provided protruding into the flexible tube. The cable tie is then suitably positioned below the barb. There are some drawbacks related to the use of cable ties in this context. One problem is that the compression of the flexible tube will not be evenly distributed over the whole circumference because of the head of the cable tie. Under the head of the cable tie the flexible tube will "bubble up" and this could cause leakage. If mold insert lines from the molding process also are present at the same location as the cable tie head the leakage problem could even be aggravated. Another problem is that the strap of the cable tie which is left pointing out from the head after tightening is somewhat sharp, particularly if it is the remaining part of a cut-off strap, and could possibly damage sensitive materials provided in vicinity. Often one needs to wrap the cable ties in bubble wrap to avoid damage. Still a further problem with the use of cable ties is that it is rather time consuming. The positioning and tightening of one cable tie can take around 1-2 minutes and in a typical bioprocessing environment there could be hundreds of such connections to be done.

A connection clamping device is described in for example U.S. Pat. No. 7,090,257, hereby incorporated by reference in its entirety. This connection clamping device comprises two parts which need to be threaded onto the flexible tube and then a tool is needed to fit these two parts over each other in order to compress the flexible tube over the tube connector. One problem with this device is that these parts need to be slid over the flexible tube which can be tricky, especially since one of them fits close to the tube, i.e. the inner diameter of one of the parts is almost the same as the tube outer diameter. Furthermore, the use of a tool is both tricky, it needs some force and precision, and time consuming.

SUMMARY

An object of the invention is to provide an improved connection clamping device for securing flexible tubes to tube connectors.

A further object of the invention is to provide a connection clamping device that is easy to connect and reliable, i.e. leak proof and steady.

A yet further object of the invention is to provide a connection clamping device which does not risk damaging bag films and other sensitive materials in a disposable bioprocess assembly. This should be done without time-consuming application (and subsequent removal) of protective wrappings.

This is achieved in a connection clamping device arranged for securing a flexible tube to a barbed end of a tube connector, whereby the barbed end comprises a barb and the tube connector during connection is arranged to protrude into an end of the flexible tube. According to the invention, the connection clamping device comprises two sections which, during connection when the tube connector protrudes into an end of the flexible tube, are arranged to be connected and locked to each other by a locking mechanism around the tube connector and the flexible tube, such that the flexible tube is compressed against the tube connector by a rib provided on the inner circumference of the connection clamping device. Alternatively expressed, the connection clamping device is arranged to secure a flexible tube to a barbed end of a tube connector when in a clamped (closed) position, wherein the externally exposed surfaces of the connection clamping device in a clamped (closed) position are rounded and without sharp corners to prevent damage to bioprocess disposables such as flexible bags.

Hereby a connection clamping device for securing tubes to tube connectors is achieved that is fast and easily mounted with high precision and which seals the connection evenly over the whole circumference, without risking damage of sensitive disposables.

This is also achieved in a method for securing a flexible tube to a tube connector, said method comprising the steps of:
providing the tube connector protruding into an end of the flexible tube;
providing a connection clamping device around the flexible tube and the tube connector when the tube connector protrudes into the tube, said connection clamping device comprises two sections which are connected and locked to each other during this step;
squeezing the flexible tube against the tube connector by a rib provided on a part of the inner surface of the connection clamping device around the circumference.

Hereby a method is achieved by which flexible tubes can be fast and easily connected to tube connectors with high precision and whereby a reliable connection is achieved.

The objective of the invention is further achieved by a disposable bioprocess assembly, comprising at least one flexible bioprocess bag with at least one port comprising a tube connector, wherein a flexible tube is connected to the tube connector and secured with a connection clamping device.

Yet further, the objective is achieved by a method for bioprocessing, which comprises the steps of:
a) providing a flexible bioprocess bag with one or more ports comprising tubing connectors;

b) connecting one or more flexible tubes to the tubing connectors such that the tubing connectors protrude into the ends of the flexible tubes;
c) securing the flexible tubes to the tubing connectors by applying connection clamping devices around the tubes and forcing the connection clamping devices into a clamped position;
d) folding the flexible bioprocess bag for shipment;
e) unfolding the bag;
f) conveying a liquid into the bag and running a bioprocess.

Embodiments of the invention are described in the dependent claims.

DETAILED DESCRIPTION OF EMBODIMENTS

Figure 1A:
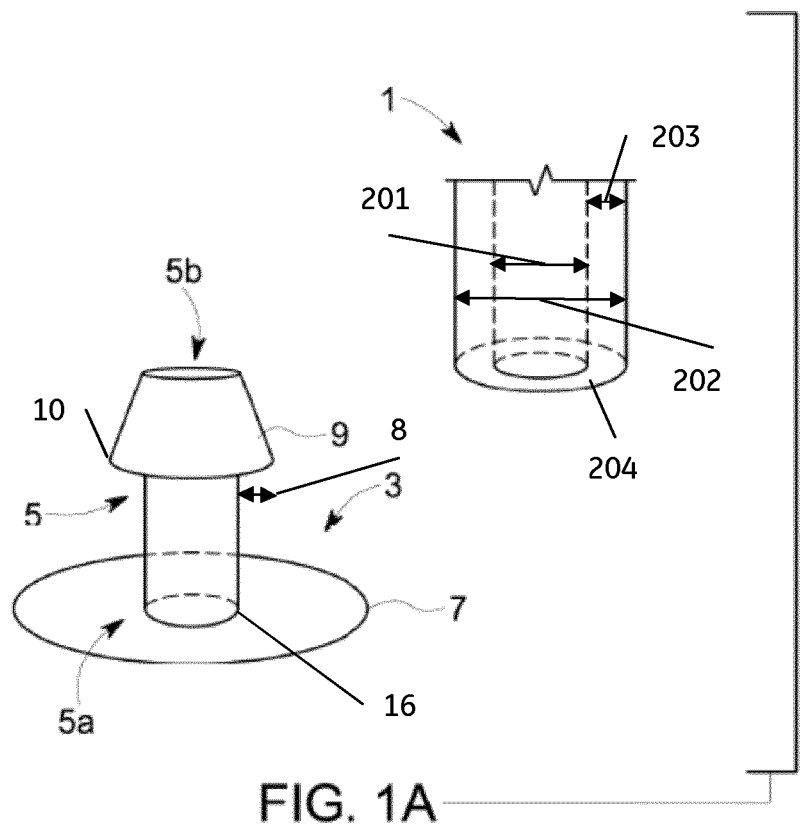
FIG. 1a shows schematically a flexible tube and a port.

FIG. 1a shows schematically a flexible tube 1, with inner diameter 201, outer diameter 202, wall thickness 203 and tube end 204, and a port 3. This kind of port 3 could be provided onto for example bags that need to be connected to other components such as flexible tubes. When connecting the flexible tube 1 to the port 3 the tube is simply slid over a tube connector 5 of the port 3. The tube connector 5 of the port 3 has the form of a short tube and is connected to a sealing part 7 of the port 3 in a first (proximal) end 5a of the tube connector 5. The sealing part 7 of the port 3 is in this embodiment shown to extend around the first end 5a of the tube connector 5 in a perpendicular direction to the tube extension. The sealing part is adapted to be sealed, e.g. by welding, to the device that should be connected to the flexible tube 1, such as for example a flexible bioprocess bag. A second (distal) end 5b of the tube connector 5, which is positioned on the other end of the tube connector 5 compared to the first end 5a, usually comprises a barb 9. This end is also called a barbed end 5b of the tube connector 5. An outside diameter of the tube connector 5 is typically close to but slightly bigger than an inner diameter 201 of the flexible tube. A flexible tube to be connected to a tube connector typically needs to be stretched to be slid over the barb and the tube connector. Hereby no gap is provided between the tube connector and the flexible tube.

Figure 1B:
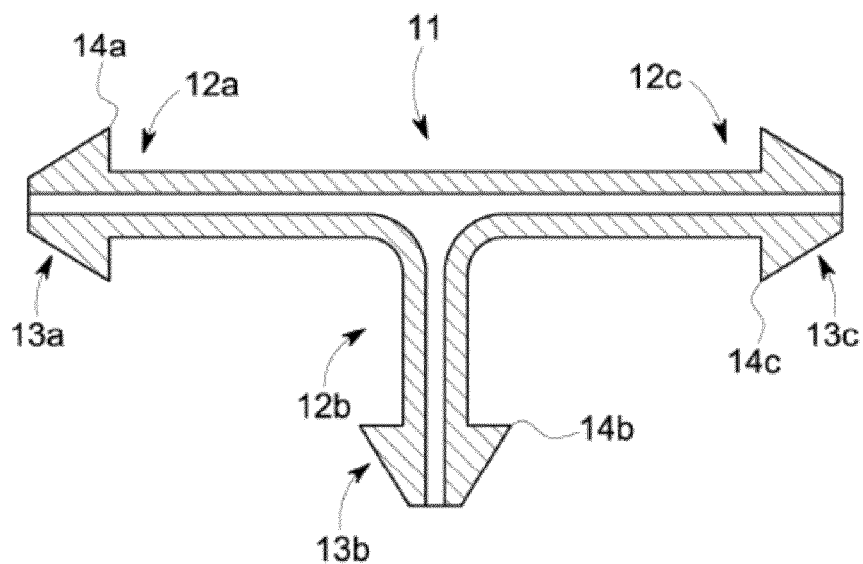
FIG. 1b shows schematically a coupling.

FIG. 1b shows schematically a coupling 11. This is a so-called T coupling. Such a coupling can for example couple sensors, couplings, fittings and pumps. Other types of coupling such as Y couplings can also be used in this invention. The T coupling comprises three tube connectors 12a, 12b, 12c pointing in different directions and being internally connected to each other. Each of the tube connectors 12a, 12b, 12c comprises a barbed end 13a, 13b, 13c, i.e. a barb 14a, 14b, 14c is provided towards the end of each of the tube connector 12a, 12b, 12c. Flexible tubes are provided over the barbed ends during connection. This is further shown in FIG. 7.

FIGS. 2a, 10-13 and 16 show schematically connection clamping devices 21;221;421 according to certain embodiments of the invention, in open (FIGS. 2a and 10) and closed (clamped) (FIGS. 11-13,16) positions. The connection clamping device 21;221;421 comprises a first section 23a; 223a;423a and a second section 23b;223b;423b. The two sections 23a;223a;423a, 23b;223b;423b are each in the form of complementary tube parts, e.g. half tubes, i.e. when the two sections 23a;223a and 23b;223b are connected to each other a tube formed (tubular) device is provided. Each section 23a;223a;423a, 23b;223b;423b of the connection clamping devices 21;221;421 has an inner surface 25;225; 425 and an outer surface 27;227;427 where inner and outer refer to inner and outer surface when the two sections are connected and a tubed formed device is provided. Each section 23a;223a;423a, 23b;223b;423b also has a first connection surface 29a;229a, 29a';229a' and a second connection surface 29b;229b, 29b';229b'. These connection surfaces 29a;229a, 29a';229a', 29b;229b, 29b';229b' of the two sections 23a;223a;423a, 23b;223b;423b are the surfaces contacting each other when the two sections are connected and form a tube formed part. In these embodiments, the two sections 23a;223a;423a, 23b;223b;423b are connected to each other via a hinge 31;231 that can be a living hinge provided between the second connection surfaces 29b;229b, 29b';229b' of the two sections. Hereby the device is provided as one single part. The first connection surfaces 29a;229a, 29a';229a' comprise a snap locking mechanism. In these embodiments, there is shown one 233 or two 33a, 33b protruding latches on the first connection surface 29a';229a' of the second section 23b;223b and one 234 or two 34a, 34b corresponding recesses on the first connection surface 29a; 229a of the first section 23a;223a. The protruding latches 233;33a, 33b each comprise a latch barb 235;35a, 35b and correspondingly the recesses 234;34a, 34b are designed such that a snapping locking is achieved when the protruding latches 233;33a, 33b with their barbs 235;35a, 35b are provided into the recesses 234;34a, 34b. The number of latches and recesses can be varied. The design of the locking mechanism can be varied such as for example the use of a hook.

According to the invention a first part 41a;241a;441a of a first rib is provided along the inner surface 25;225;425 of the first section 23a;223a;423a and a second part 41b;241b; 441b of a first rib is provided along the inner surface 25;225;425 of the second section 23b;223b;423b. The first and second parts of the first rib 41a;241a;441a, 41b;241b; 441b are provided in a circumferential direction and will connect to the rib of the other section when the two sections 23a;223a;423a, 23b;223b;423b are connected such that a first rib is provided around the whole circumference of the inner surface of the tube formed part. The first and second parts of the first rib 41a;241a;441a, 41b;241b;441b are here shown to be in the form of a semi-circle 41a, 41b or raised semi-circle (semi-circle on top of a rectangle) 241a, 241b revolved along the circumference of the inner surface 25;225;425. However, the rib could also be in another form such as rectangular or with a triangular cross section. The function of the first rib 41a;241a;441a, 41b;241b;441b is that it should protrude into the flexible tube when securing the tube to the port. The penetration depth of the rib into the flexible tube wall may e.g. be at least 10% of the wall thickness 204, such as at least 20% or 20-50% of the wall thickness. This can be achieved by proper selection of the inner diameter 205 of the rib for a tube 1 of given outer 202 and inner 201 diameter. The rib should be provided in such a position on the connection clamping device such that the rib is provided below (behind) a barb of the tube connector, i.e. between the barb edge 10 and the proximal end 5a of the tube connector, to be connected to the flexible tube.

According to some embodiments of the invention the inner diameter 206 of the connection clamping device 21;221;421 when the two sections 23a;223a;423a, 23b; 223b;423b are connected is slightly larger than the outer diameter 202 of the flexible tube (except from the location of the first rib). Hereby the only part of the connection clamping device 21;221;421 that is touching the flexible tube may be the first rib 41a;241a;441a, 41b;241b;441b. The first rib 41a;241a;441a, 41b;241b;441b will compress the flexible tube as discussed above and thereby compress the tube to the tube connector as is the purpose of the invention. Because of the small empty space between the rest of the connection clamping device inner diameter 206 and the outside diameter 202 of the flexible tube any bubbling up of the tube as a consequence of the rib compressing and displacing the tube can be housed in this empty space without any additional forces on the locking mechanism. Hereby also the installation is easier and requires less force.

Figure 2A:
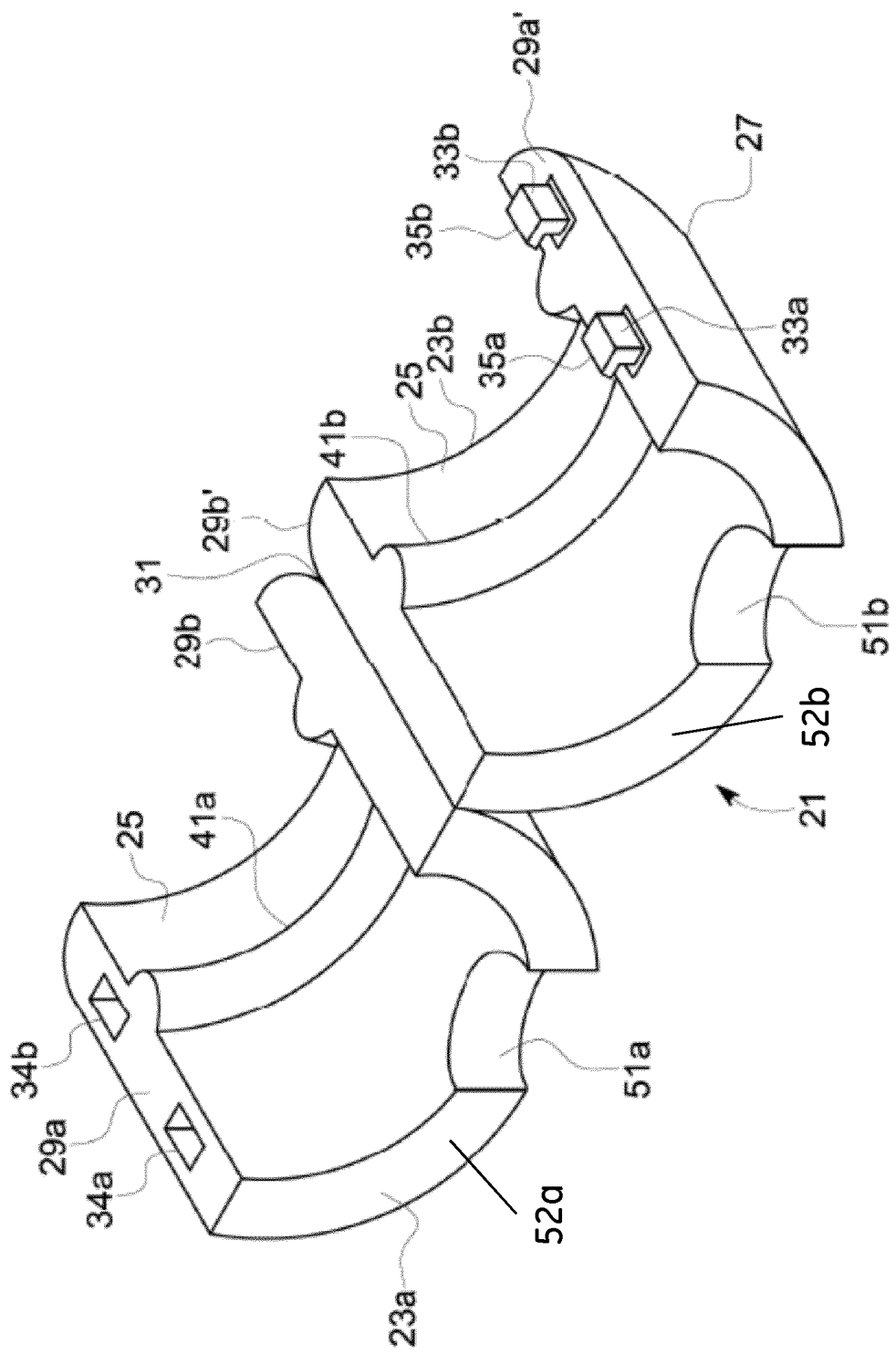
FIG. 2a shows schematically a connection clamping device according to one embodiment of the invention in an open position.
Figure 10:
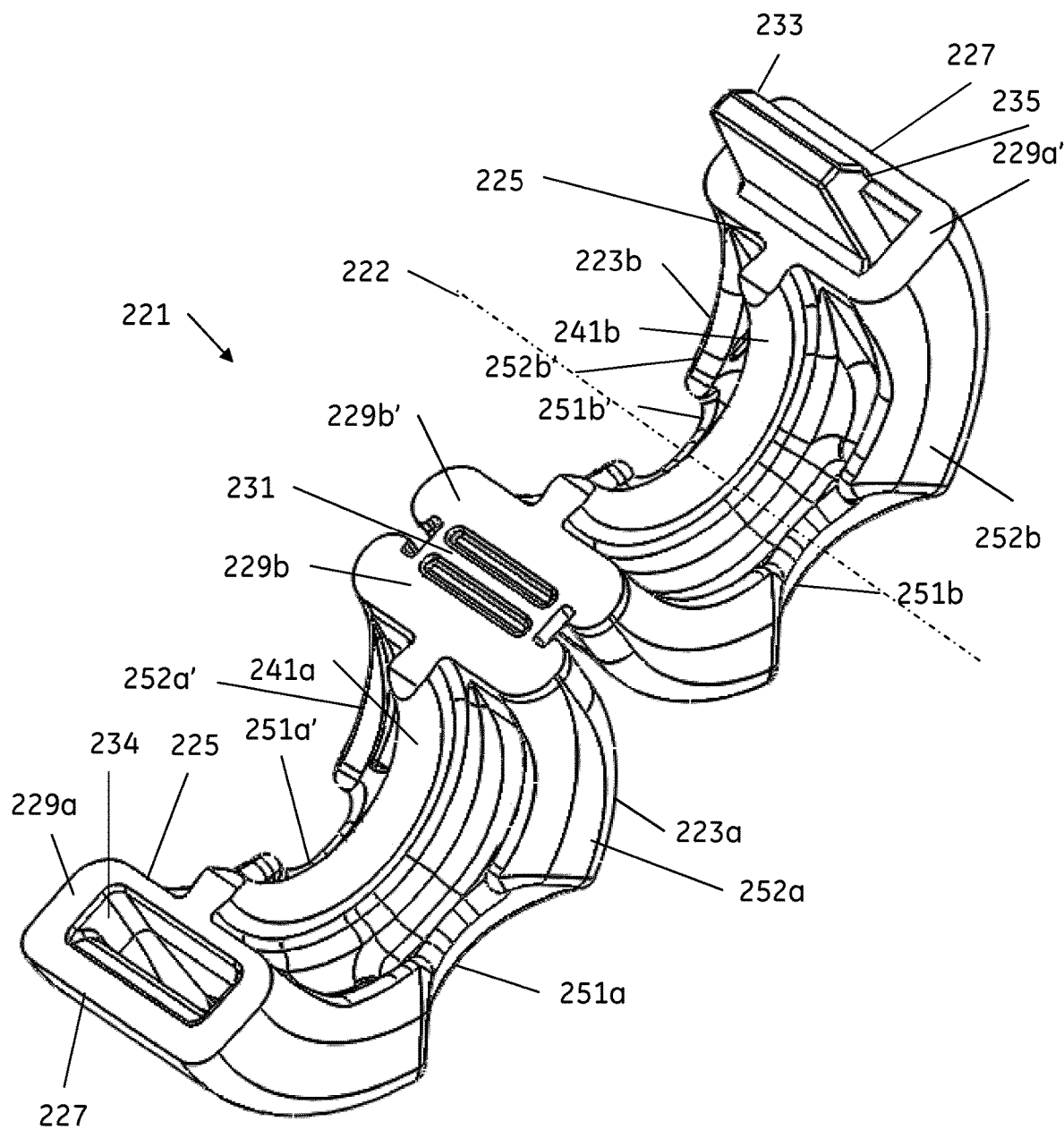
FIG. 10 shows schematically an embodiment of a connection clamping device according to the invention in open position.
Figure 11:
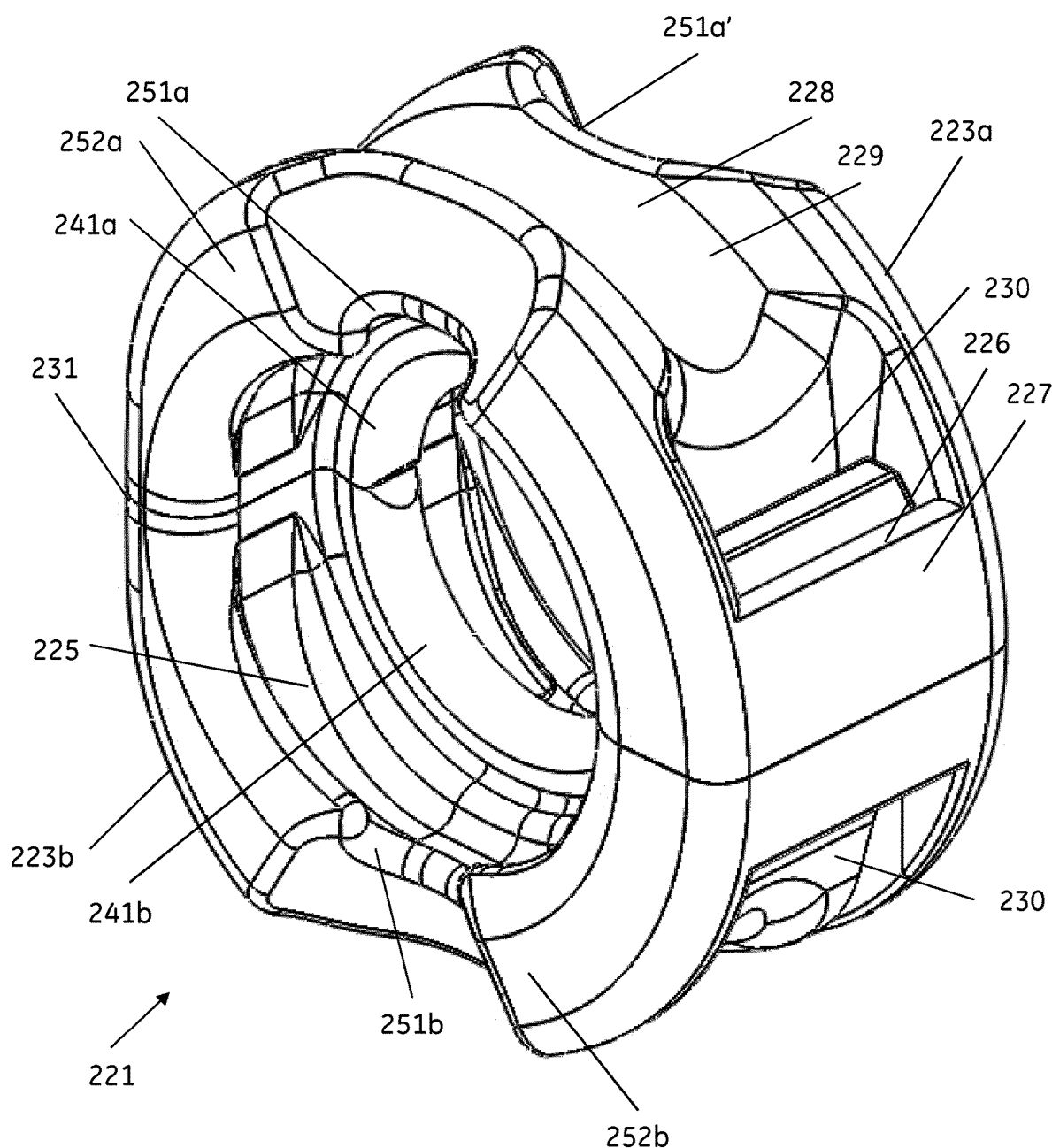
FIG. 11 shows the connection clamping device of FIG. 10 in a closed position.
Figure 12:
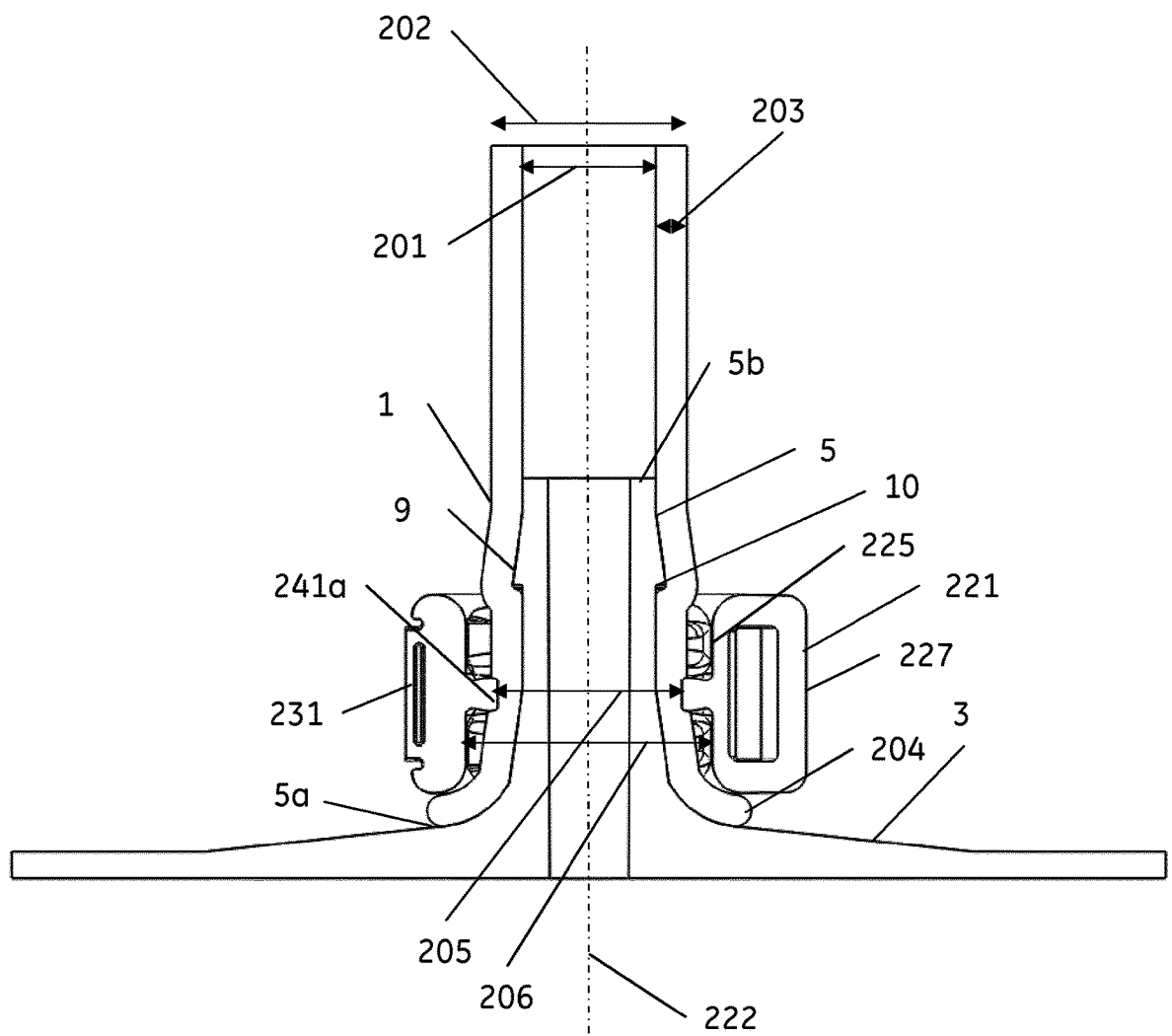
FIG. 12 shows schematically in cross section the connection clamping device of FIGS. 10 and 11, securing a tube on a tube connector.

In certain embodiments of the invention there is one or more indicator recess 51a;251a,251a', 51b;251b,251b' provided either in one of the two sections 23a;223a, 23b;223b or as shown in FIGS. 2a and 10-11 in both the first and the second section 23a;223a, 23b;223b. The indicator recess 51a;251a,251a', 51b;251b,251b' is a recess or window in the wall of the sections, at least on that side of the sections that will be provided opposite to the barbed end of the tube connector during connection. When the connection clamping device 21;221 has been positioned over the flexible tube and the tube connector for securing them together, the end 204 of the tube should be seen (or mechanically detected) through an indicator recess 51a;251a,251a', 51b;251b,251b' adjacent the proximal end 5a. This ensures that the tube has been positioned correctly over the tube connector. During use it can also always be checked that the tube still is in place by looking through the indicator recess. For example, if the tube has been pulled by mistake it can easily be checked that the tube is still in a correct position over the tube connector by only checking that the tube can be seen through the indicator recess 51a;251a,251a', 51b;251b,251b'. The indicator recess/recesses 51a;251a,251a', 51b;251b,251b' can suitably extend in a longitudinal direction from an end wall 52a,52a';252a 252a', 52b,52b';252b,252b' of one or both of the two sections 23a;223a, 23b;223b. In some embodiments, indicator recesses 51a,51b,51a',51b' may extend from both a first 52a, 52b and a second 52a', 52b' end wall of one or both of the two sections 23a;223a, 23b;223b. This allows the construction of a connection clamping device 221, which is symmetric around a plane orthogonal to a longitudinal axis 222 of the device and which will have an indicator recess adjacent the proximal end 5a irrespective of its direction. Such a device can be applied to a tube connector plus tube irrespective of its direction, which allows for simpler mounting and it also facilitates automated mounting.

In some embodiments, the connection clamping device 221 comprises one or more (such as two) plier recesses 230 extending inwards from the outer surface 227 of a side wall of one or both of the two sections 223a,223b. The plier recess(es) can suitably be located near (adjacent) the first connection surfaces 229a, 229a' of the two sections, allowing for application of a suitable closing force by a closing tool. The closing tool can be a pair of pliers or similar, but it can also be any other tool capable of urging the first connection surfaces together. Suitably, each plier recess comprises a tool/plier application surface 226, which may be substantially parallel to one of the first connection surfaces 229a, 229a'. Alternatively, the tool/plier application surface 226 may be shaped to correspond to a shaped engaging surface of a particular closing tool/plier to be used.

Figure 13:
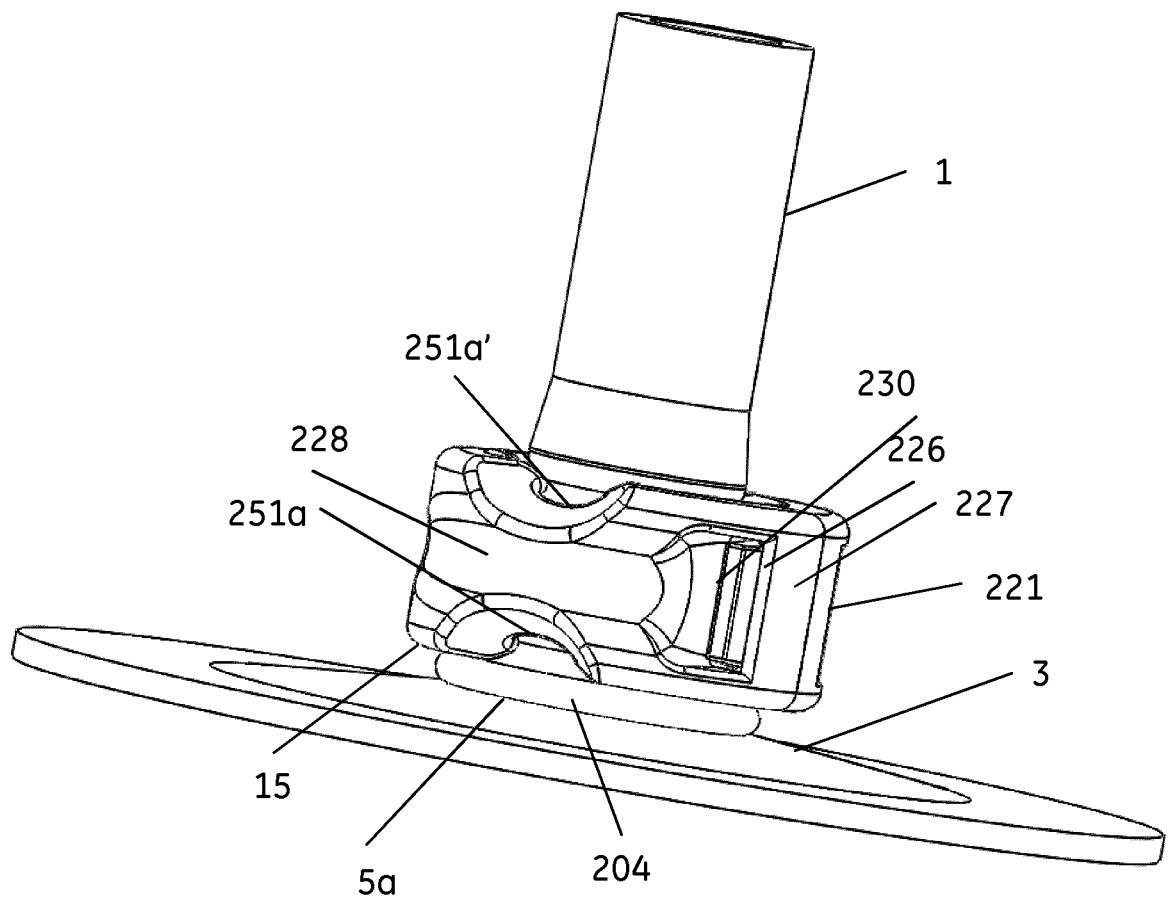
FIG. 13 shows the connection clamping device of FIGS. 10 and 11, securing a tube on a tube connector.
Figure 14:
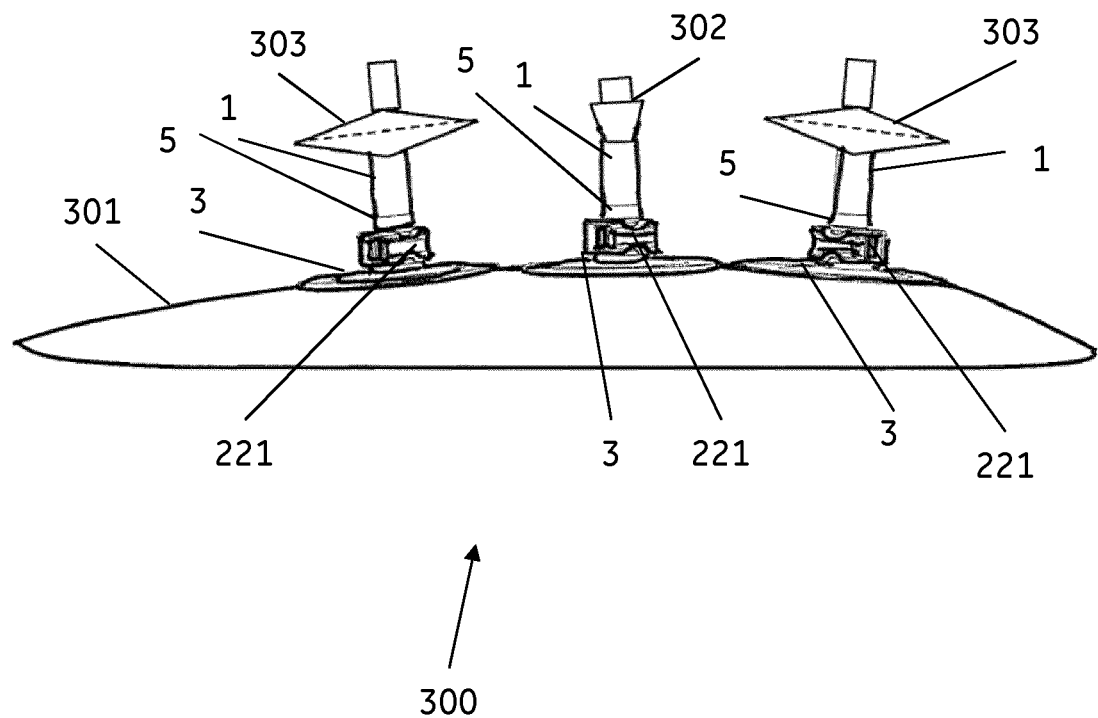
FIG. 14 shows a flexible bag with ports, tube connectors and tubes secured by connection clamping devices of the invention.

In certain embodiments, the connection clamping device 221 has a recessed waist portion 228. The waist recess 229 can extend from the outer surfaces 227 of the two sections and can facilitate gripping of the device as well as facilitating the application of the closing tool to the plier recess(es) 230, which can suitably be located in the recessed waist portion. The waist recess 229 may extend all around the side wall or, as illustrated in FIGS. 11 and 13, only around one or more part (sector) of the side wall.

Figure 16:
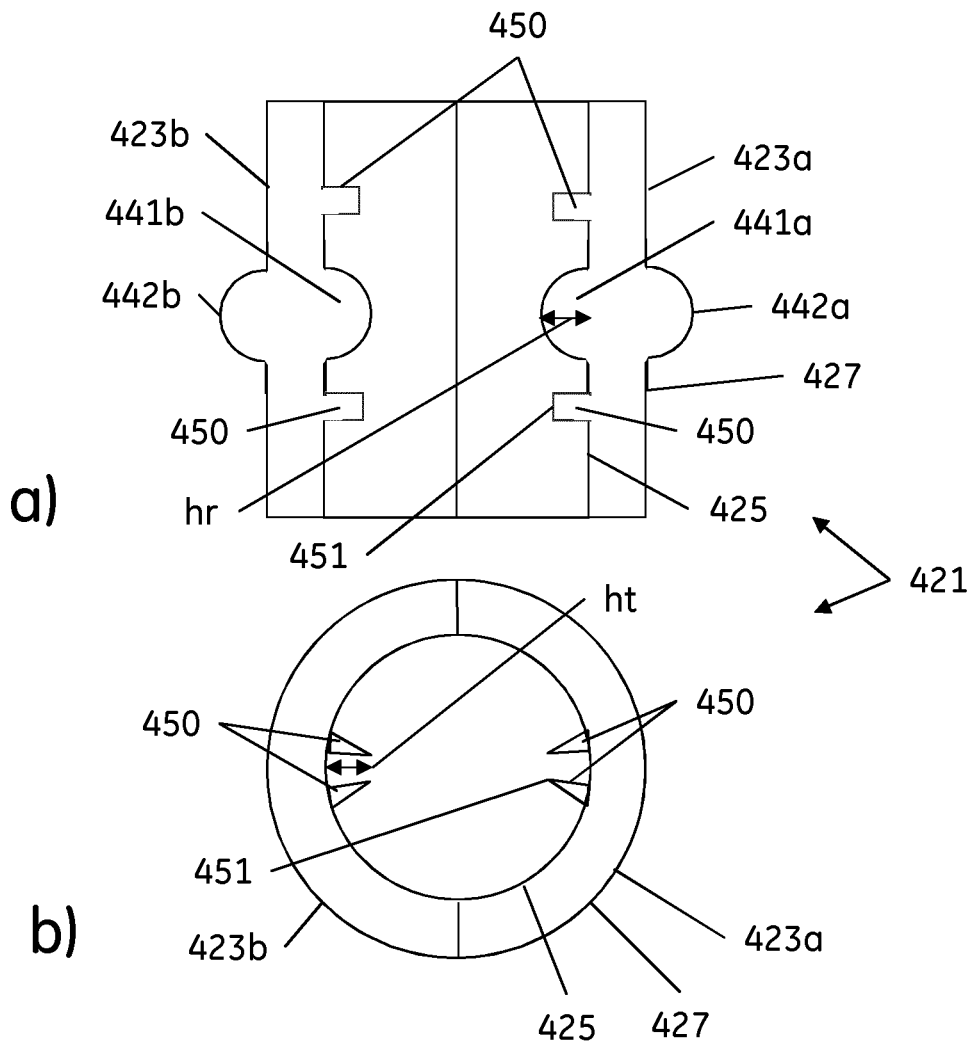
FIG. 16 shows a connection clamping device with anti-rotation teeth and an external rib, a) side view and b) end view.

In some embodiments, as illustrated by FIG. 16, the connection clamping device 421 further comprises one or more anti-rotation teeth 450, protruding from the inner surface 425. The anti-rotation teeth are arranged to engage the flexible tube and prevent rotation of the connection clamping device 421 around the tube when in the closed position. The anti-rotation teeth 450 may extend radially inwards from inner surface 425, with a tooth height ht. The tooth height ht can suitably be less than the rib height hr, such as 60-90% of hr. The anti-rotation teeth can suitably have an edge 451 at a distal end of the teeth in relation to the inner surface 425, arranged to penetrate into the flexible tube. The number of anti-rotation teeth can vary, but can e.g. be at least 2, such as 4 or 8, e.g. located pairwise on both sides of first and second rib 441*a* and 441*b*. The connection clamping device 421 may additionally or alternatively comprise first and second external rib 442*a* and 442*b*, protruding from the outer surface 427. The first and second external rib 442*a* and 442*b* can be located opposite to first and second rib 441*a* and 441*b* and may be of similar dimensions as first and second rib 441*a* and 441*b*.

Figure 2B:
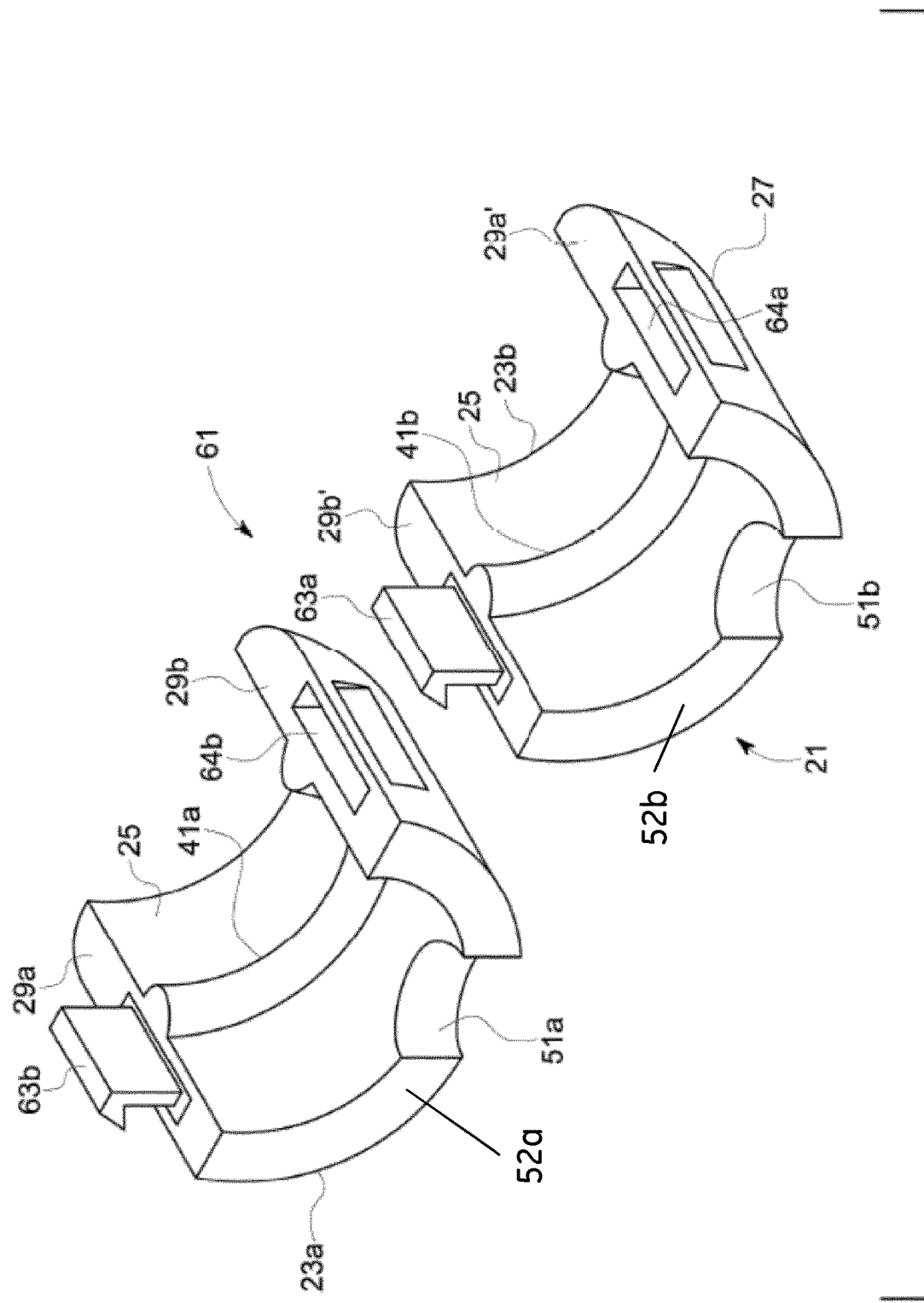
FIG. 2b shows schematically a connection clamping device according to another embodiment of the invention in an open position.

FIG. 2*b* shows schematically a connection clamping device 61 according to another embodiment of the invention, in an open position. The difference from the connection clamping device 21 shown in FIG. 2*a* is only that there is no hinge connecting the two sections 23*a*, 23*b*. Most of the reference numbers are the same as in FIG. 2*a* and the description will not be repeated. Instead of a hinge connecting the two second connection surfaces 29*b*, 29*b*' a snap locking mechanism corresponding to the snap locking mechanism on the first connection surfaces 29*a*, 29*a*' is provided also to the second connection surfaces 29*b*, 29*b*'. In this embodiment one protruding latch 63*a* is provided on the second connection surface 29*b*' of the second section 23*b* and one protruding latch 63*b* is provided on the first connection surface 29*a* of the first section 23*a* and correspondingly one recess 64*a* is provided in the first connection surface 29*a*' of the second section 23*b* and one recess 64*b* is provided in the second connection surface 29*b* of the first section 23*a*. As discussed above the number of latches and recesses can be chosen.

Figure 3A:
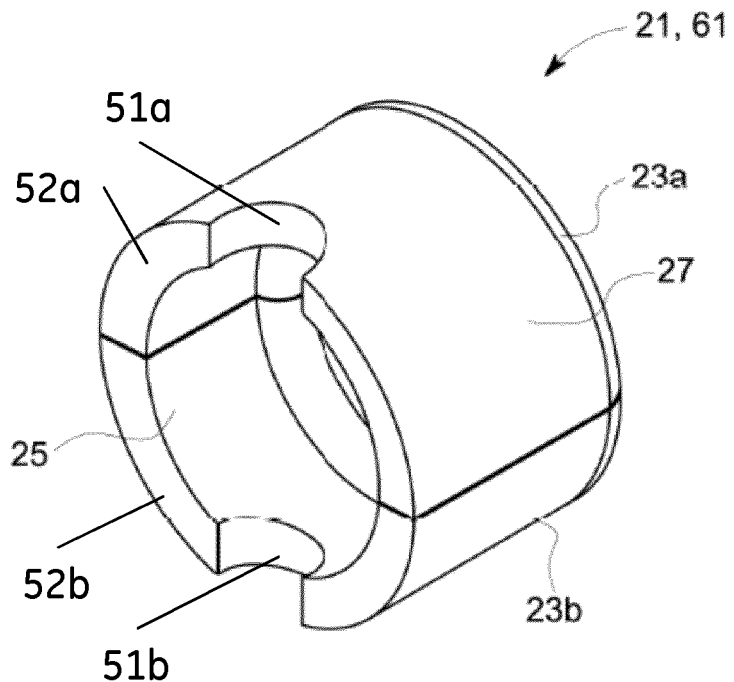
FIG. 3a shows the connection clamping device of FIG. 2a or 2b in a closed position.
Figure 3B:
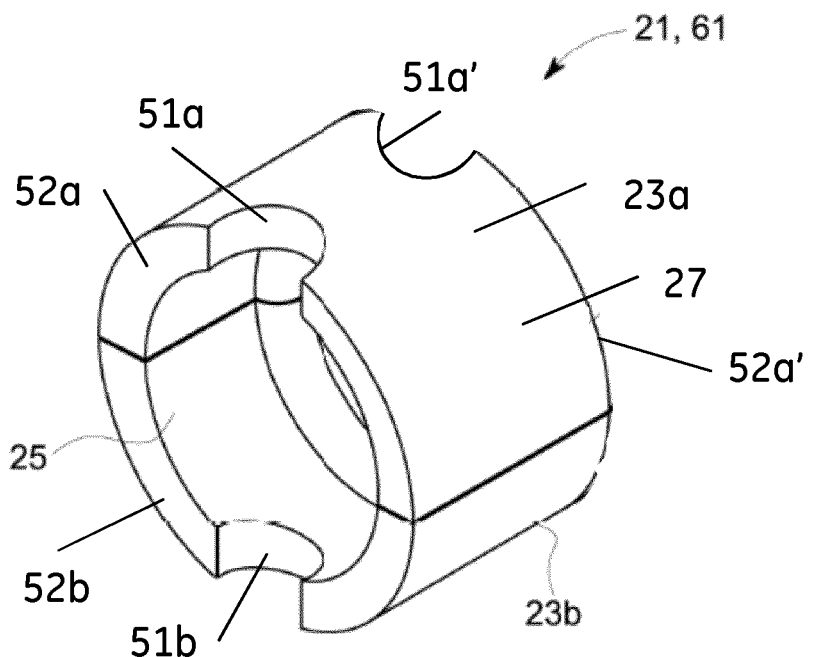
FIG. 3b shows a connection clamping device having inspection recesses at both end walls.

FIG. 3 shows the connection clamping device of FIG. 2*a* or 2*b* in a closed (clamped) position. Hereby the latches 33*a*, 33*b*, 63*a*, 63*b* have been provided into the recesses 34*a*, 34*b*, 64*a*, 64*b* and provide a snap locking mechanism. A short tube is formed with an outer surface 27 and an inner surface 25.

Figure 4:
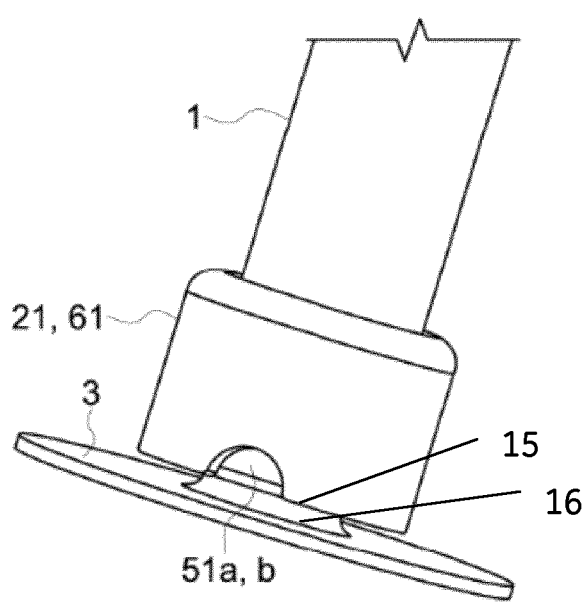
FIG. 4 shows the connection clamping device of FIG. 2a or 2b in closed position over the flexible tube and tube connector hereby securing the flexible tube to the tube connector.

FIG. 4 shows the connection clamping device 21, 61 of FIG. 2*a* or 2*b* in closed (clamped) position over a flexible tube 1 and a tube connector 5 of a port 3 hereby securing the flexible tube to the port. Here it can be seen through the indicator recess 51*a* or 51*b* that the flexible tube 1 is in correct position. It can also be seen that the outer surface of the connection clamping device 21, 61 is smooth, with rounded externally exposed edges/surfaces typically having radii of curvature above 0.5 mm, such as above 1 mm or even above 2 mm, and will not damage any other components in the vicinity.

Figure 5A:
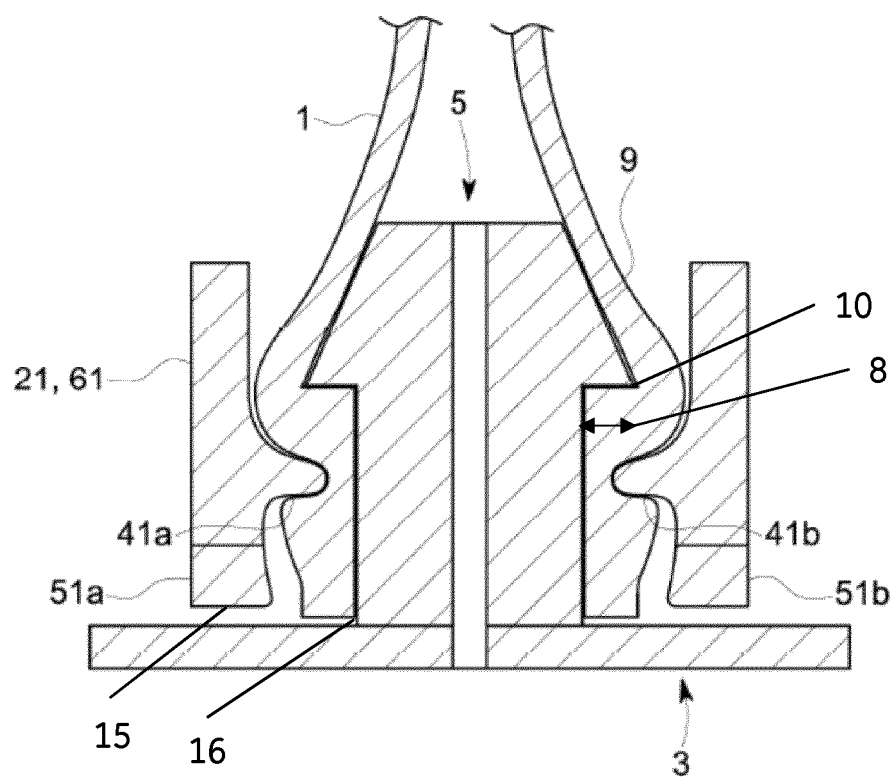
FIG. 5a shows schematically FIG. 4 in cross section.

FIG. 5*a* shows FIG. 4 in cross section. Here a tube connector 5 of a port 3 as defined in relation to FIG. 1 can be seen. The tube connector also has a barb 9, with a barb edge 10 and a barb height 8. A flexible tube 1 is shown connected to the port 3 and a connection clamping device 21, 61 as described in relation to the FIGS. 2-4 is shown in connection position. The rib 41*a*, 41*b* is shown to compress the tube against the tube connector 5 of the port 3 below the barb 9, i.e. between the barb edge 10 and the proximal end 5*a*. The indicator recesses 51*a*, 51*b* are also shown.

Figure 5B:
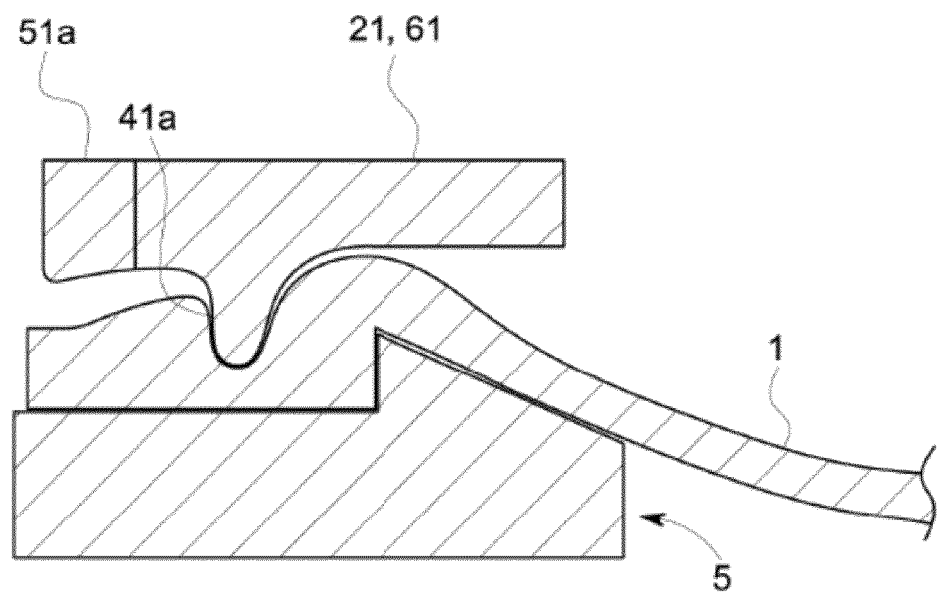
FIG. 5b shows schematically an enlarged view of the compression of the tube.

FIG. 5*b* shows schematically an enlarged view of the compression of the tube. Tube displacement can be seen. It can also be seen that the gap provided between the connection clamping device and the tube in all places except from where the rib is provided can house the tube displacement—or tube bubble up caused by the compressing of the tube from the rib.

Figure 6A:
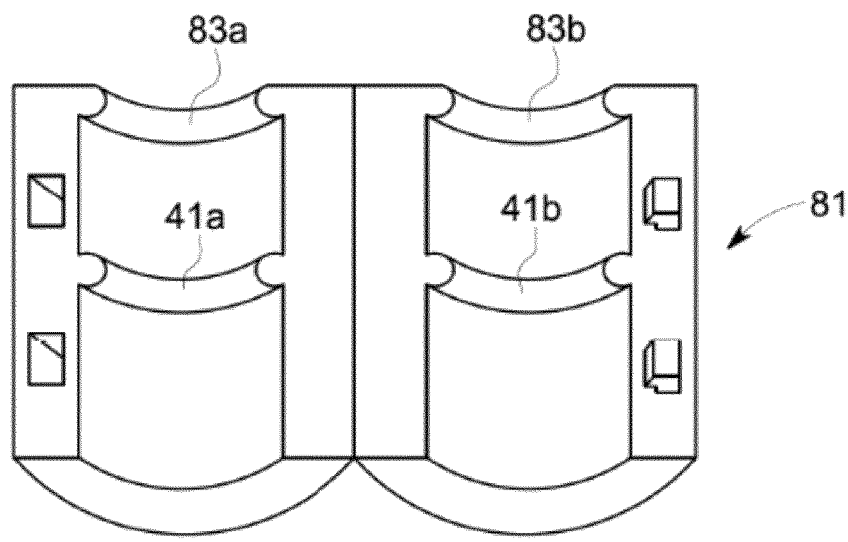
FIG. 6a shows schematically a connection clamping device according to another embodiment of the invention in an open position.

FIG. 6*a* shows schematically a connection clamping device 81 according to another embodiment of the invention in an open position. Almost all the details are exactly the same as in the embodiment shown in FIG. 2*a* so the reference numbers will be the same and the description will not be repeated. The difference is that in this embodiment a second rib 83*a*, 83*b* is provided in addition to the first rib 41*a*, 41*b*. This second rib 83*a*, 83*b* is provided in the end of the first and second sections 23*a*, 23*b* and is arranged to squeeze the tube against the tube connector 5 just above the barb 9. This can be seen in FIG. 6*b*.

Figure 6B:
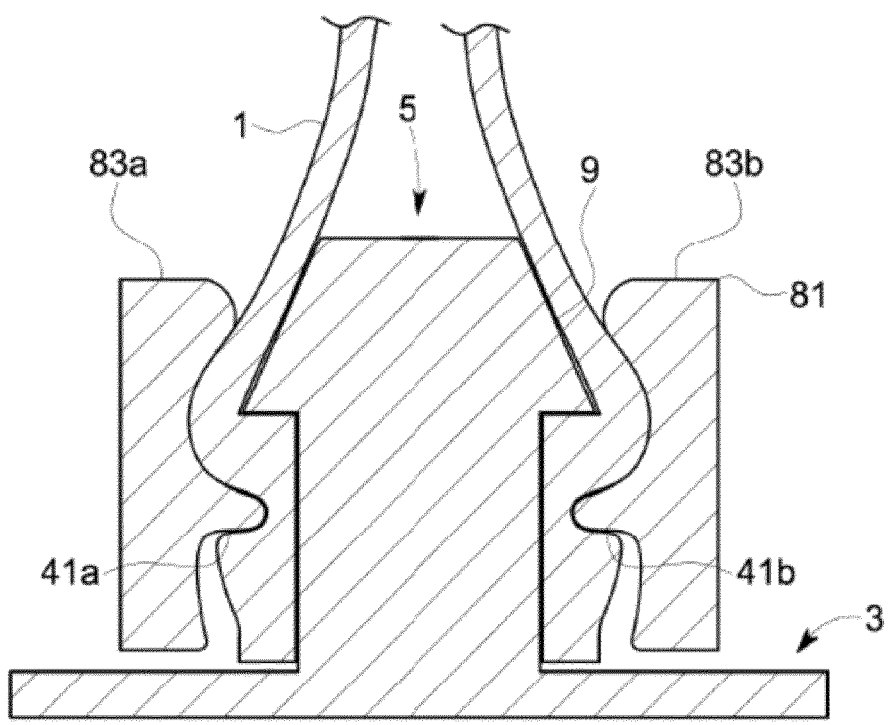
FIG. 6b shows schematically the connection clamping device of the embodiment of FIG. 6a in connected position and in cross section.

FIG. 6*b* shows schematically the connection clamping device 81 of the embodiment of FIG. 6*a* in connected position and in cross section. The first rib 41*a*, 41*b* is shown to squeeze the flexible tube 1 against the tube connector 5 of the port 3 below the barb 9 and the second rib 83*a*, 83*b* is shown to squeeze the flexible tube 1 against the tube connector 5 of the port 3 above the barb 9. An advantage with this embodiment is that it can take higher pressure. Furthermore this embodiment seals in a location (the cone area) that doesn't need to have mold insert lines. This makes the seal more reliable. Suitably, this embodiment can include a feature that aligns the connection clamping device with the tube connector in the axial direction. This feature is further shown and described in relation to FIG. 9. This feature will ensure that the second rib will seal against the coned surface of the barb.

Different sizes of the connection clamping device can be provided for different tube and tube connector sizes, to achieve suitable compression as discussed above. Different sizes could suitably be colored differently or otherwise optically coded, e.g. with distinctive marks, symbols, bar codes etc. Such optical or colour codes can be provided on the connection clamping device but also on one or more of the tube connector and the tube to be used in a particular connection. This is particularly useful when a particular bioprocess assembly to be manufactured comprises tubes of different outer diameters and/or tube connectors of different diameters and the operator rapidly has to select the proper connection clamping device for a given position.

Figure 7:
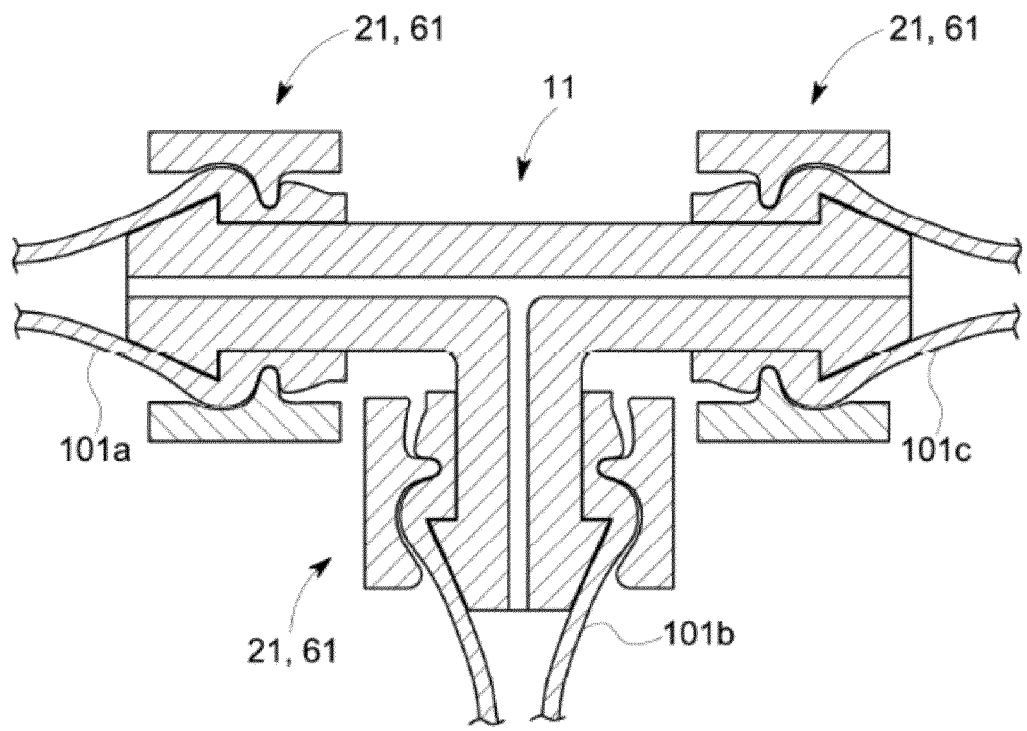
FIG. 7 shows schematically in cross section three flexible tubes connected by the use of three connection clamping devices according to the invention to a T coupling.

FIG. 7 shows schematically in cross section three flexible tubes 101*a*, 101*b*, 101*c* connected to a T coupling 11 (as shown in FIG. 1*b*) by the use of three connection clamping devices 21, 61 according to the invention.

Figure 8:
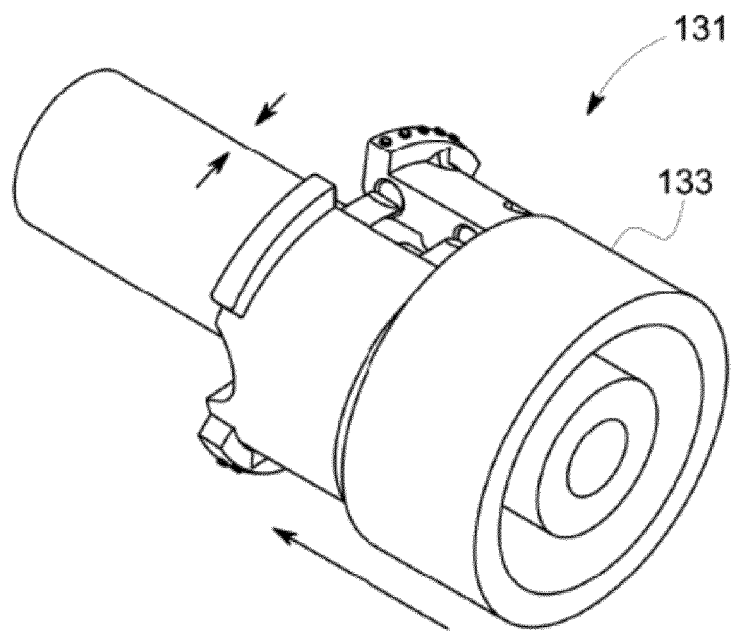
FIG. 8 shows schematically another embodiment of a connection clamping device according to the invention.

FIG. 8 shows schematically another embodiment of a connection clamping device 131 according to the invention. A different type of locking mechanism is provided instead of the latches and recesses described in relation to FIGS. 2*a* and 2*b*. In this embodiment the locking mechanism is a resilient sleeve 133 to be slid over the two sections when connected over the tube and tube connector. In this Figure it is shown to be two separate sections but they could also be hinged to each other. The outer surface of the two sections could be provided with a means, such as a recess or a pattern for receiving such a sleeve.

Figure 9:
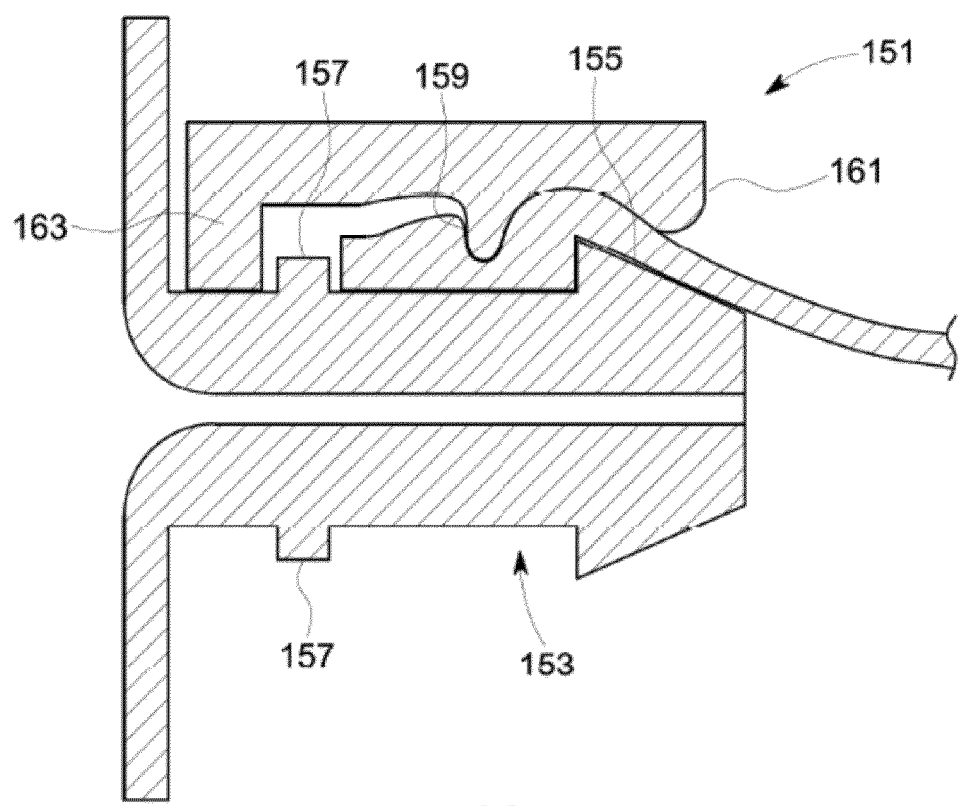
FIG. 9 shows schematically in cross section another embodiment of a connection clamping device according to the invention.

FIG. 9 shows schematically in cross section another embodiment of a connection clamping device 151 according to the invention. In this embodiment also the tube connector 153 needs to be adapted. The tube connector 153 is provided as usual with a barb 155 in one end but according to this embodiment there is also provided a tube connector rib 157 in the other end. This tube connector rib 157 is provided for keeping the connection clamping device 151 in correct position and for providing a first and a second rib 159, 161 (even more ribs could be provided) in correct sealing positions. For this purpose, a positioning rib 163 is provided outermost in one of the ends of the connection clamping device 151. This is the end which will be provided opposite to the barbed end of the tube connector when the securing clamping means is applied. The positioning rib 163 and the tube connector rib 157 will when the connection clamping device is provided be adjacent each other and assure the position of the connection clamping device. The positioning rib 163 does not need to be a rib over the whole circumference. It can instead be for example two or more rib parts provided one in each section of the connection clamping device. An advantage with this embodiment is that the second rib of the connection clamping device can be assured to be provided sealing against the cone part of the barb. It could be suitable to seal against the cone part of the barb because this part may not comprise any mold insert lines.

Further, according to the invention, a method for securing a flexible tube 1 to a tube connector 5 is provided. The method comprises the steps of:

- providing the tube connector protruding into an end 204 of the flexible tube, e.g. such that the tube end 204 is adjacent a proximal end 5a of the tube connector. The tube connector can suitably be barbed, with a barb edge 10 and having a barb height 8. The barb edge may be sharp, e.g. with a radius of curvature 0.3 mm or lower, such as 0.2 mm or lower. The barb height may e.g. be at least 0.4 mm, such as at least 0.5 mm, 0.4-2 mm or 0.5-1.5 mm;
- providing a connection clamping device 21; 61; 81; 131; 151; 221 (e.g. as described above) around the flexible tube and the tube connector 5 when the tube connector protrudes into the tube 1, said connection clamping device comprises two sections 23a;223a, 23b;223b which are connected and locked to each other during this step;
- squeezing the flexible tube against the tube connector by a rib 41a;241a, 41b;241b provided on a part of the inner surface 25;225 of the connection clamping device around the circumference. The rib can suitably be located such that it squeezes the tube behind a barb edge 10 (between barb edge 10 and proximal end 5a), e.g. with a penetration depth as discussed above. This step can suitably be performed by forcing the connection clamping device into a clamped position with a tool engaging at least one, such as two, plier recesses 230 in a side wall of the connection clamping device.

As described above, the connection clamping device may be optically coded, such as colour coded, to indicate the compatibility with the tube and tube connector and the method may then comprise a step of selecting a connection clamping device compatible with the tube and tube connector based on the optical or colour coding. At least one of the tube and the tube connector may also be optically coded, such as colour coded, to indicate the compatibility with the connection clamping device, the tube and/or the tube connector.

After the squeezing step, the method may comprise a step of verifying that the tube is properly secured to the tube connector. This step may e.g. comprise verifying that the optical or colour coding of the connection clamping device is correct. It may further comprise verifying that the optical or colour coding of the connection clamping device conforms with an optical or colour coding of the tube and/or tube connector.

Additionally, or alternatively, the verification step may comprise verifying, through an indicator recess at a proximal end 15 of the connection clamping device, that an end 204 of the tube is located adjacent to a proximal end 5a of the tube connector, i.e. that the tube extends all the way to the proximal end ("bottom") of the tube connector.

In a further aspect, the invention discloses a disposable bioprocess assembly 300, which comprises at least one flexible bioprocess bag 301 with at least one port 3 (e.g. several ports) having a tube connector 5, wherein one or more flexible tube 1 is connected to the tube connector(s) and secured with one or more connection clamping device 21; 61; 81; 131; 151; 221, e.g. one or more connection clamping device as discussed above.

The flexible bioprocess bag may comprise a plurality of ports and these ports may have tubing connectors of at least two different outer diameters. A plurality of flexible tubes can be connected to the tube connectors and secured with connection clamping devices of at least two different sizes (corresponding to the particular tubes and tube connectors) and the connection clamping devices of different sizes can be differently optically coded, such as differently colour coded.

As discussed above, the externally exposed surfaces of the connection clamping device(s) in a clamped position can be rounded and without sharp corners, to prevent damage to the flexible bioprocess bag and any other sensitive components.

Figure 15:
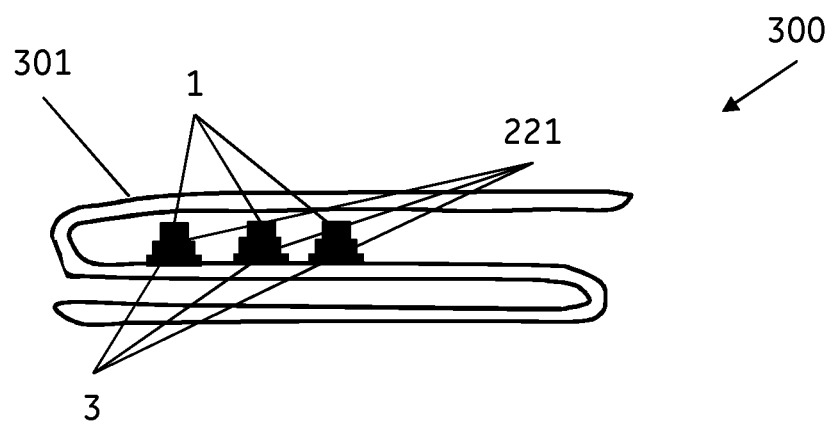
FIG. 15 shows a folded flexible bag with ports, tube connectors and tubes secured by connection clamping devices of the invention.

The flexible bioprocess bag can be folded and packaged for shipment (FIG. 15) and it may also be presterilized, e.g. by radiation (e.g. gamma ray) sterilization. The disposable bioprocess assembly can suitably be closed, with aseptic barriers towards the outer environment. For connection to further devices, the assembly may comprise one or more aseptic connectors (not shown), e.g. ReadyMate™ or similar connectors, one or more aseptic access ports 302, e.g. Clave™ Port or similar ports, one or more tubes with sterile filters 303 and/or one or more closed tubes amenable to sterile welding connection.

In a yet further aspect, the invention discloses a method for bioprocessing. This method comprises the steps of:

a) providing a flexible bioprocess bag 301 with one or more ports 3 comprising tube connectors 5;
b) connecting one or more flexible tubes 1 to the tube connectors such that the tubing connectors protrude into the ends 204 of the flexible tubes, e.g. such that ends 204 are adjacent the proximal ends 5a of the tube connectors;
c) securing the flexible tubes to the tube connectors by applying one or more connection clamping devices 21; 61; 81; 131; 151; 221 (e.g. connection clamping devices as discussed above) around the tubes and forcing the connection clamping devices into a clamped position;
d) folding the flexible bioprocess bag for shipment;
e) unfolding the bag;
f) conveying a liquid into the bag and running a bioprocess.

The method may further comprise, before step e), a step d') of sterilizing the flexible bioprocess bag and the flexible tubes. Such a step may comprise exposing the bag and the tubes to ionizing radiation, e.g. gamma radiation with a radiation dose known in the art to achieve sterilization, e.g. about 15-25 kGy or higher. The flexible bioprocess bag and the flexible tubes can form a disposable bioprocess assembly, optionally together with other components such as filters, ports etc. For connection to further devices, the assembly may comprise one or more aseptic connectors (not shown), e.g. ReadyMate™ or similar connectors, one or more aseptic access ports 302, e.g. Clave™ Port or similar ports, one or more tubes with sterile filters 303 and/or one or more closed tubes (not shown) amenable to sterile welding connection.

The externally exposed surfaces of the connection clamping devices in a clamped position can suitably be rounded and without sharp corners, as discussed above, to prevent damage to the flexible bioprocess bag.

This written description uses examples to disclose the invention, including the best mode, and also to enable any person skilled in the art to practice the invention, including making and using any computing system or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A connection clamping device for bioprocess disposables, arranged to secure a flexible tube to a barbed end of a tube connector, the barbed end comprising a barb and the tube connector during connection being arranged to protrude into an end of the flexible tube,
   wherein said connection clamping device comprises a first section and a second section which, during connection when the tube connector protrudes into an end of the flexible tube, are arranged to be connected and locked to each other in a clamped position by a locking mechanism around the tube connector and the flexible tube, such that the flexible tube is compressed against the tube connector by a rib provided on the inner circumference of the connection clamping device,
   wherein said connection clamping device further comprises one or more anti-rotation teeth protruding inward from an inner surface, wherein said one or more anti-rotation teeth has a tooth height less than a height of said rib, and
   wherein the externally exposed surfaces of said connection clamping device in a clamped position are rounded and do not define sharp corners or sharp edges to prevent damage to said bioprocess disposables.

2. The connection clamping device according to claim 1, wherein said connection clamping device comprises:
   a first part of the rib provided in the first section and a second part of the rib provided in the second section, which rib parts together form the rib over the inner circumference of the tube formed part when the two sections are locked together,
   wherein the first section and the second section of the connection clamping device are arranged to be positioned around and locked around the flexible tube and the tube connector when the tube connector protrudes into the tube and the first rib is arranged to squeeze the flexible tube against the tube connector below the barb provided on the tube connector.

3. The connection clamping device according to claim 1, wherein an inner diameter of the connection clamping device except from where the rib is provided is larger than an outer diameter of the flexible tube and an inner diameter of the tube formed part at the position for the rib is less than the outer diameter of the flexible tube.

4. The connection clamping device according to claim 1, wherein the two sections are connected to each other on one side by a living hinge.

5. The connection clamping device according to claim 1, wherein the locking mechanism is arranged on a first connection surface of each of the two sections and the locking mechanism is one or more protruding latches on one of the sections and recesses on the other of the two sections.

6. The connection clamping device according to claim 1, wherein the locking mechanism is arranged on both a first and a second connection surface of each of the two sections and the locking mechanism is one or more protruding latches on one of the sections and recesses on the other of the two sections.

7. The connection clamping device according to claim 1, wherein an indicator recess is provided in a side wall of one or both of the two sections.

8. The connection clamping device according to claim 7, wherein said indicator recess extends from an end wall of one or both of the two sections.

9. The connection clamping device according to claim 8, comprising indicator recesses extending from both a first and a second end wall of one or both of the two sections.

10. The connection clamping device according to claim 1, which is symmetrical around a transverse plane.

11. The connection clamping device according to claim 1, wherein the rib is a first rib, wherein a second rib is provided in the two sections, and
    wherein the second rib is arranged to compress the flexible tube against a coned surface of the barb when the connection clamping device is provided for clamping the tube to the tube connector.

12. The connection clamping device according to claim 1, characterized in that it comprises a positioning rib arranged to counteract with a tube connector rib for aligning the connection clamping device axially with the tube connector.

13. The connection clamping device according to claim 1, further comprising one or more plier recesses in a side wall of one or both of the two sections.

14. The connection clamping device according to claim 1, wherein each of the two sections has a side wall having a recessed waist portion.

15. The connection clamping device according to claim 1, which is arranged to secure a flexible tube of particular inner and outer diameters to a tube connector of corresponding outer diameter and which is optically coded to indicate the compatibility with said tube and tube connector.

16. The connection clamping device according to claim 1, further comprising a first and a second external rib protruding from an outer surface.

17. The connection clamping device according to claim 1, wherein the anti-rotation teeth comprise an edge at a distal end of the teeth arranged to penetrate into the flexible tube.

18. The connection clamping device according to claim 1, wherein said rib of the connection clamping device is the only rib provided on the inner circumference of the connection clamping device.

* * * * *